(12) United States Patent
Cawthon

(10) Patent No.: US 8,048,631 B2
(45) Date of Patent: Nov. 1, 2011

(54) REDUCING NON-TARGET NUCLEIC ACID DEPENDENT AMPLIFICATIONS: AMPLIFYING REPETITIVE NUCLEIC ACID SEQUENCES

(75) Inventor: Richard Cawthon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 12/700,475

(22) Filed: Feb. 4, 2010

(65) Prior Publication Data

US 2010/0151477 A1    Jun. 17, 2010

Related U.S. Application Data

(62) Division of application No. 10/355,626, filed on Jan. 31, 2003, now Pat. No. 7,695,904.

(60) Provisional application No. 60/353,591, filed on Jan. 31, 2002.

(51) Int. Cl.
    *C12Q 1/68*   (2006.01)
    *C12P 19/34*  (2006.01)
    *C07H 21/04*  (2006.01)

(52) U.S. Cl. .................... 435/6.12; 435/92.2; 536/24.33

(58) Field of Classification Search .................. None
    See application file for complete search history.

*Primary Examiner* — Samuel Woolwine
(74) *Attorney, Agent, or Firm* — Ballard Spahr LLP

(57) ABSTRACT

The present invention provides for compositions and methods for amplifying target nucleic acids using nucleic acid primers designed to limit non-target nucleic acid dependent priming events. The present invention permits amplifying and quantitating the number of repetitive units in a repetitive region, such as the number of telomere repetitive units.

21 Claims, 3 Drawing Sheets

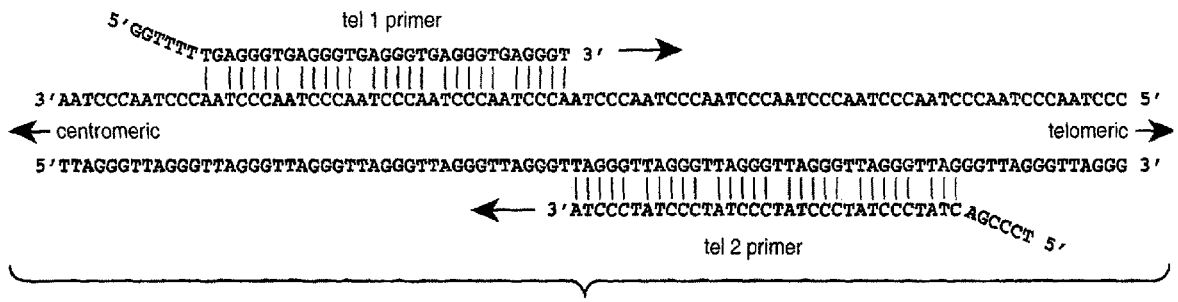
FIG._1A
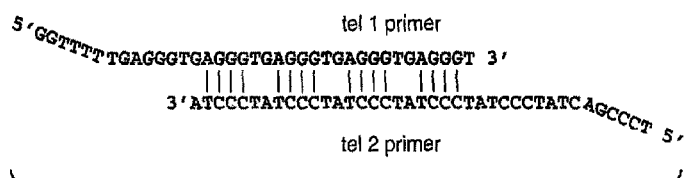
FIG._1B

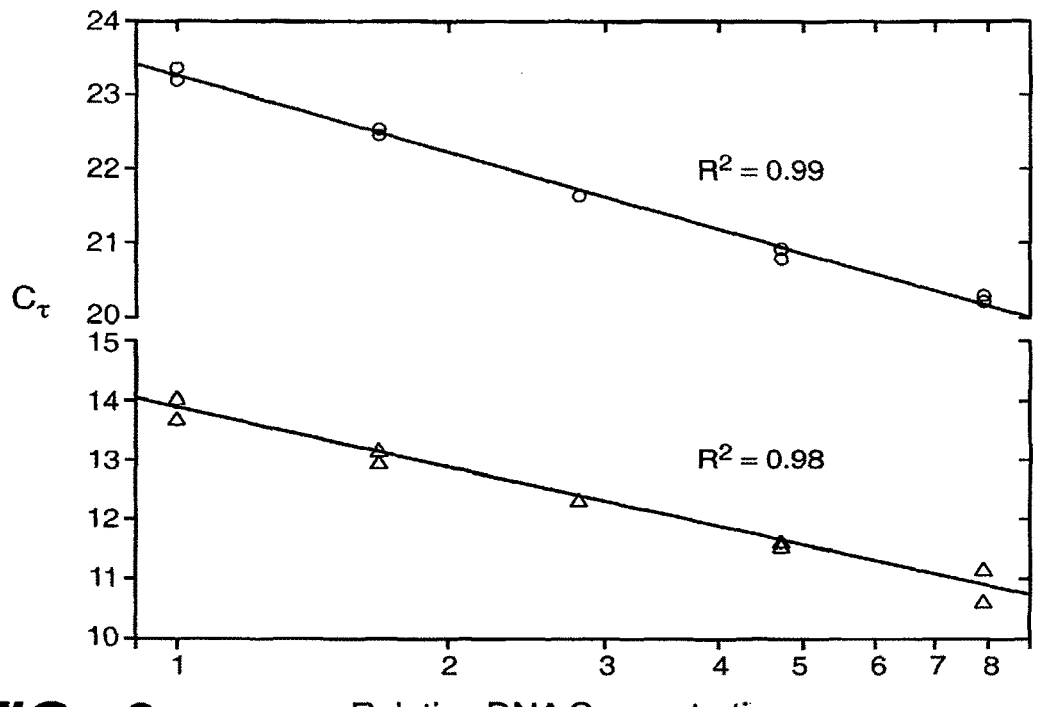
FIG._2
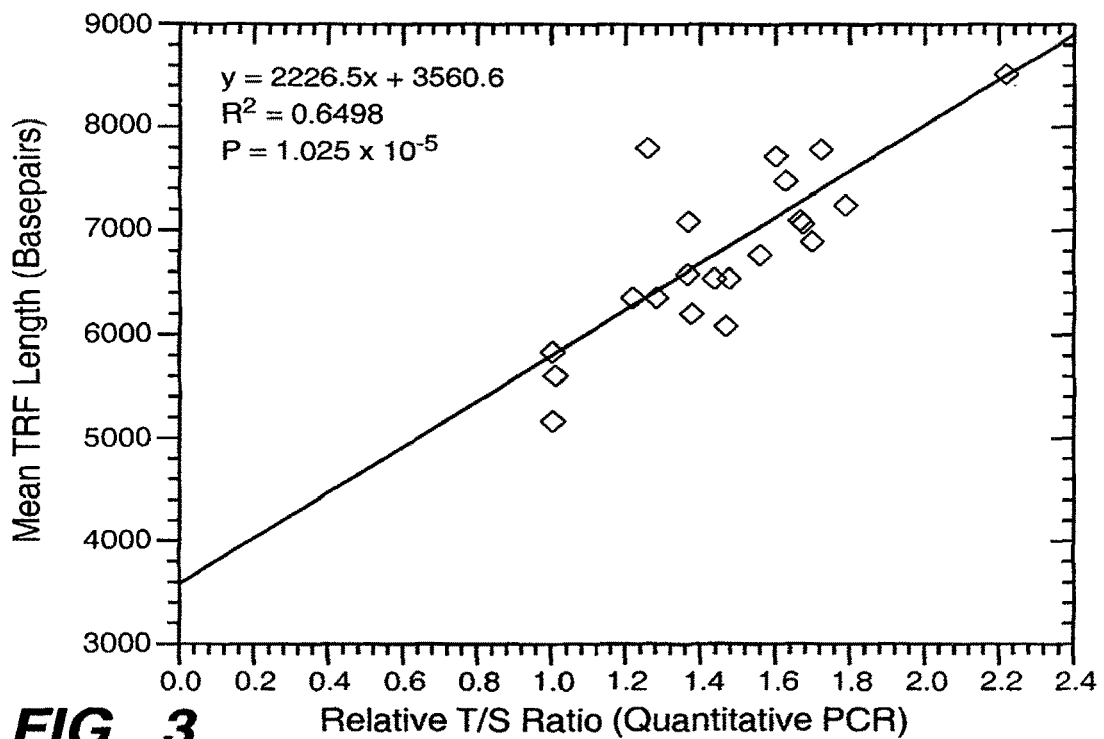
FIG._3

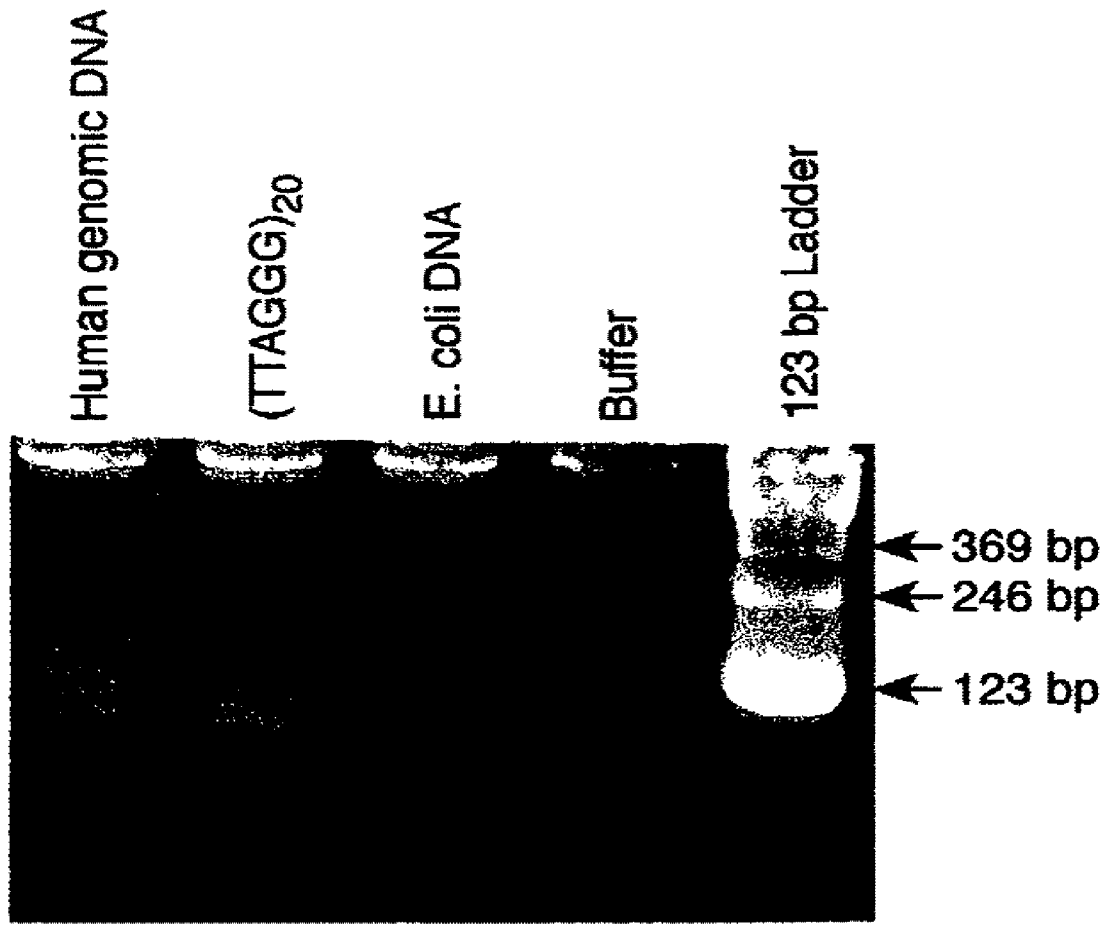
FIG._4

SEQUENCE LISTING

<160> NUMBER OF SEQ ID NOS: 10

<210> SEQ ID NO 1
<211> LENGTH: 37
<212> TYPE: DNA
<213> ORGANISM: Artificial sequence
<220> FEATURE:
<223> OTHER INFORMATION: Synthetic primer

<400> SEQUENCE: 1 ggttttgag ggtgagggtg agggtgaggg tgagggt                37

-continued

```
<210> SEQ ID NO 2
<211> LENGTH: 39
<212> TYPE: DNA
<213> ORGANISM: Artificial sequence
<220> FEATURE:
<223> OTHER INFORMATION: Synthetic primer

<400> SEQUENCE: 2
tcccgactat ccctatccct atccctatcc ctatccta                              39

<210> SEQ ID NO 3
<211> LENGTH: 90
<212> TYPE: DNA
<213> ORGANISM: Human

<400> SEQUENCE: 3
ccctaaccct aaccctaacc ctaaccctaa ccctaaccct aaccctaacc ctaaccctaa      60
ccctaaccct aaccctaacc ctaaccctaa                                      90

<210> SEQ ID NO 4
<211> LENGTH: 90
<212> TYPE: DNA
<213> ORGANISM: human

<400> SEQUENCE: 4
ttagggttag ggttagggtt agggttaggg ttagggttag ggttagggtt agggttaggg      60
ttagggttag ggttagggtt agggttaggg                                      90

<210> SEQ ID NO 5
<211> LENGTH: 120
<212> TYPE: DNA
<213> ORGANISM: human

<400> SEQUENCE: 5
ttagggttag ggttagggtt agggttaggg ttagggttag ggttagggtt agggttaggg      60
ttagggttag ggttagggtt agggttaggg ttagggttag ggttagggtt agggttaggg     120

<210> SEQ ID NO 6
<211> LENGTH: 23
<212> TYPE: DNA
<213> ORGANISM: human

<400> SEQUENCE: 6
cagcaagtgg gaaggtgtaa tcc                                             23

<210> SEQ ID NO 7
<211> LENGTH: 25
<212> TYPE: DNA
<213> ORGANISM: human

<400> SEQUENCE: 7
cccattctat catcaacggg tacaa                                           25

<210> SEQ ID NO 8
<211> LENGTH: 39
<212> TYPE: DNA
<213> ORGANISM: Artificial sequence
<220> FEATURE:
<223> OTHER INFORMATION: Synthetic primer

<400> SEQUENCE: 8
cggtttgttt gggtttgggt tgggtttgg gtttgggtt                             39
```

```
<210> SEQ ID NO 9
<211> LENGTH: 39
<212> TYPE: DNA
<213> ORGANISM: Artificial sequence
<220> FEATURE:
<223> OTHER INFORMATION: Synthetic primer

<400> SEQUENCE: 9
ggcttgcctt acccttaccc ttacccttac ccttaccct                                   39

<210> SEQ ID NO 10
<211> LENGTH: 42
<212> TYPE: DNA
<213> ORGANISM: human

<400> SEQUENCE: 10
ttagggttag ggttagggtt agggttaggg ttagggttag gg                               42
```

REDUCING NON-TARGET NUCLEIC ACID DEPENDENT AMPLIFICATIONS: AMPLIFYING REPETITIVE NUCLEIC ACID SEQUENCES

CROSS-REFERENCE TO RELATED PATENT APPLICATIONS

This application claims benefit of U.S. patent application Ser. No. 10/355,626 filed Jan. 31, 2003, now U.S. Pat. No. 7,695,904, which claims priority to U.S. Provisional Patent Application No. 60/353,591.

STATEMENT REGARDING FEDERALLY SPONSORED RESEARCH OR DEVELOPMENT

This invention was made with government support under Grant Number K01 AG 00767 awarded by the National Institutes of Health. The Government has certain rights to this invention.

FIELD OF THE INVENTION

The invention relates to the field of recombinant DNA technology. Specifically, the present invention is drawn to compositions and methods for amplifying target nucleic acids, especially direct amplification of repetitive nucleic acid sequences.

BACKGROUND OF THE INVENTION

Detecting the presence of target nucleic acids is vital in numerous applications in medical diagnostics, forensics, genetic analysis, and public health. For instance, identifying specific DNA sequences is critical for diagnosing inherited disorders, determining susceptibility to disease, and identifying causal agents of infectious diseases. Polymerase chain reaction (PCR) provides a highly sensitive method for detecting the presence of target nucleic acids by selective amplification of target nucleic acids. The method relies on use of oligonucleotide primers that hybridize to opposite ends of a target nucleic acid segment, an amplicon, and prime copying of the nucleic acid segment by a polymerase. Reiterative rounds of DNA synthesis, denaturation, and reannealing allows exponential amplification of a given target nucleic.

Primer selection is a major determinant in the success or failure of the amplification reaction. Critical factors include primer length, melting temperature ($T_m$), sequence specificity, complementary primer sequences, G/C content, and 3'-terminal region sequence. In general, primers must hybridize with specificity to the target nucleic acid but not hybridize to and amplify non-target nucleic acid sequences.

Amplifying non-target nucleic acids becomes problematic when the 3' end of a primer is complementary to another primer. These primers will tend to hybridize to each other, which are then extended by polymerase to form "primer-dimer" products. Subsequent amplification of primer-dimers leads to depletion of primers, resulting in reduced sensitivity or even failure to amplify the intended target nucleic acid. Performing primer extensions or preamplification annealing at temperatures limiting primer-primer hybrids (e.g., "hot start" PCR, D'Aquila, R. T. et al., Nucleic Acids Res. 19: 3749 (1991); "touchdown" PCR, Don, R. H. et al., Nucleic Acids Res. 19: 4008 (1991)) or adjusting buffer components to increase hybridization stringency may minimize primer-dimer interference. However, the presence of excess primers during PCR reactions allows even weak complementarity at the 3' terminal region to generate these interfering side products.

Although choosing different regions of the target nucleic acid for selecting primers provides a basis for limiting non-target nucleic acid dependent amplifications, constraints on selecting sequences for generating primers can limit the choice of alternative primer designs. For example, directly amplifying short, tandem repetitive sequences such as telomere repeats is difficult since the primers for these sequences will always have some degree of complementarity. These repetitive sequences do not normally afford a choice in primer sequences for limiting formation of primer-dimer products. Consequently, current methods for estimating telomere lengths rely on restriction enzyme digestion of genomic DNA followed by hybridization with repeat sequences (terminal restriction fragment analysis; see Harley, C. B. et al, Nature 345: 458-460 (1990)), indirect amplification of repeats using unique sequences positioned outside of the repeat region (see Kozlowski, M. R. et al., U.S. Pat. No. 5,741,677), fluorescence in situ hybridization (see Henderson, S. J. Cell Biol. 134: 1-12 (1996)), or flow cytometry methods (see Hultdin, M. Nucleic Acids Res. 26: 3651-3656 (1998)). Generally, these procedures are time consuming or require substantial quantities of DNA. Since the copy number of telomere repeats and other tandemly repetitive sequences in a cell correlate with the physiological or diseased states of a cell, there is a need for compositions and methods for rapidly amplifying and quantitating these sequences while generally avoiding competing primer-dimer side reactions during amplification.

SUMMARY OF THE INVENTION

In accordance with the objects outlined above, the present invention provides methods for amplifying target nucleic acids while limiting non-target nucleic acid dependent amplifications. In a preferred embodiment, the method comprises contacting a target nucleic acid comprising substantially complementary first and second strands with a first and second primer, wherein the first primer hybridizes to the first strand and the second primer hybridizes to the second strand of the target nucleic acid, and wherein the hybridized primers are capable of primer extension when hybridized to their respective strands. At least one nucleotide of the first primer is altered to produce a mismatch between altered residue and the 3' terminal nucleotide residue of the second primer when first and second primers hybridize to each other. The target nucleic acid is subsequently amplified by polymerase chain reaction.

In another aspect, the method for amplifying the target nucleic acid further comprises altering at least one nucleotide residue of the second primer to produce a mismatch between the altered residue on the second primer and the 3' terminal nucleotide residue of the first primer when the primers hybridize to each other.

In another preferred embodiment, the present invention provides for methods of amplifying repetitive units in a repetitive region of a target nucleic acid. In one embodiment, the method comprises contacting a target nucleic acid comprising substantially complementary first and second strands with a first and second primer, wherein the first primer hybridizes to at least one repetitive unit of the first strand and the second primer hybridizes to at least one repetitive unit of the second strand of the target nucleic acid, and wherein the hybridized primers are capable of primer extension when hybridized to their respective strands. At least one nucleotide residue of the first primer is altered to a produce a mismatch between the altered residue and a nucleotide residue of at least one repetitive unit of the first strand, wherein the altered residue also produces a mismatch with the 3' terminal nucleotide of the second primer when first and second primers hybridize to each other. Target nucleic acids are subsequently amplified by polymerase chain reaction.

In another aspect, the method for amplifying repetitive sequences further comprises altering at least one nucleotide residue of the second primer to produce a mismatch between the altered residue and a nucleotide residue of at least one repetitive unit of the second strand, wherein the altered residue of the second primer also produces a mismatch with the 3' terminal nucleotide of the first primer when the primers hybridize to each other.

In another preferred embodiment for amplifying repetitive units in a repetitive region, the method comprises contacting the substantially complementary first and second strands with a first and second primer, wherein the first primer hybridizes to more than one repetitive unit of the first strand and the second primer hybridizes to more than one repetitive unit of the second strand of the target nucleic acid, and wherein the hybridized primers are capable of primer extension when hybridized to their respective strands. Nucleotide residues of the first primer are altered to produce mismatches between the altered residues and nucleotide residues at the identical nucleotide position of each repetitive unit of the first strand, wherein the altered residues also produce a mismatch with the 3' terminal nucleotide residue of the second primer when the first and second primers hybridize to each other. The target nucleic acids are then amplified.

In another aspect, the method for amplifying repetitive sequences further comprises altering the nucleotide residues of the second primer to produce mismatches between the altered residues and the nucleotide residue at the identical position of each repetitive unit of the second strand, wherein the altered residues of the second primer also produce mismatches with the 3' terminal nucleotide residue of the first primer when the primers hybridize to each other.

In a preferred embodiment, the present invention provides methods for determining the number of repetitive units in a repetitive region of a target nucleic acid, such as telomeres, by measuring the amount of amplified target nucleic acids. These methods find applications in cancer diagnosis and examination of cell senescence.

In accordance with the described methods, the present invention further provides compositions for amplifying the subject target nucleic acids, including telomere repetitive regions.

DESCRIPTION OF THE FIGURES

FIGS. 1A and 1B depict the sequence of the oligonucleotide primer pairs, tel 1 (SEQ ID NO: 1) and tel 2 (SEQ ID NO: 2), used to amplify human telomeric repetitive units (SEQ ID NOS: 3, 4). Shown are the hybridization schemes of the primers to the telomere repetitive sequences and hybridization of the primers to each other. The tel 1 primer can hybridize to any available complementary 31 basepair stretch along the strand of telomeric DNA oriented 5' to 3' toward the centromere. The tel 2 primer can hybridize to any complementary 33 basepair stretch along the strand oriented 5' to 3' toward the end of the chromosome. For each primer, nucleotide residues are altered to produce mismatches between the altered residue and nucleotide residues at the identical nucleotide position of each repetitive unit to which the primer hybridizes. Thus, for tel 1 and tel 2, every sixth base is mismatched. To limit primer-dimer products, the altered residues of each primer also produce a mismatch with the 3' terminal nucleotide residue of the other primer when the primers hybridize to each other, thus blocking extension by polymerase. In addition, the 5' terminal regions of the primer are designed so as to not basepair with the telomeric repeats. These noncomplementary 5' terminal region sequences prevent the 3' ends of the PCR products from initiating DNA synthesis in the middle of telomere amplification products. By designing the telomere specific primers to have similar GC content, and hence similar $T_m$s (see Example 1), undesirable amplifications are further reduced.

FIG. 2 shows standard curves used to measure relative T/S ratios, where the T/S ratio is the telomere (T) to single copy gene (S) ratio (see Example 2). Five DNA concentrations over an eight-fold range were generated by serial dilution (dilution factor .about.1.68) and aliquoted into microtiter plate wells; the final amounts per well ranged from 12.64 ng to 100 ng, with the middle quantity approximately matching that of the samples being assayed. The $C_t$ of a DNA sample is the fractional number of PCR cycles to which the sample must be subjected in order to accumulate enough product to cross a set threshold of magnitude of fluorescent signal. Any individual or pooled human DNA sample may be used to create the standard curves, as long as each assayed sample's $C_t$ falls within the range of Cts of the standard curves (O=single copy gene 36B4; Δ telomere)

FIG. 3 shows correlation of relative T/S ratios determined by real time quantitative PCR using the primers described herein and the mean telomere restriction fragment (TRF) lengths determined by traditional Southern hybridization analysis. The DNA samples used for the analysis were from blood drawn from 21 individuals. All relative T/S ratios plotted have values .gtoreq.1.0 because the initial T/S ratios determined using the standard curves have all been normalized to the lowest T/S ratio (0.69) observed among the samples. The equation for the linear regression line best fitting the data is shown.

FIG. 4 shows amplification products separated by agarose gel electrophoresis and visualized by ethidium bromide staining and UV illumination. After 25 cycles of PCR, amplified human telomere DNA appears as a smear with the highest intensity beginning at about 76 basepairs and progressively fading to background around 400 basepairs (human genomic DNA). A smear of products beginning from about 76 basepairs is also obtained when a target nucleic acid template containing a known number of human telomere repetitive units, $(TTAGGG)_{20}$ (SEQ ID NO: 5), is used in the amplification. When human genomic DNA is omitted (i.e., buffer) or replaced with *E. coli*. DNA, no product is detectable up to 25 PCR cycles. DNA length standards are shown (123 by ladder).

DETAILED DESCRIPTION OF THE INVENTION

The present invention relates to methods and compositions useful in amplifying target nucleic acids while limiting non-target nucleic acid dependent amplification reactions. Specifically, the present invention provides for primers that limit amplification of primers hybridized to each other while allowing amplification of the target nucleic acid. Generally, the primers of the present invention comprise altered or mutated nucleotide residues such that when the primers hybridize to each other, the 3' terminal residue of one primer forms a mismatch with the altered or mutated nucleotide residue on the other primer, thus preventing primer extension.

The present invention finds use in reducing PCR background and for amplifying and quantitating repetitive sequences, especially telomere repetitive sequences.

By "primer", "primer nucleic acid", "oligonucleotide primer" or grammatical equivalents as used herein is meant a nucleic acid that will hybridize to some portion of the target nucleic acid. The primers of the present invention are designed to be substantially complementary to a target sequence such that hybridization of the target sequence and the primers of the present invention occurs, and proper 3' base pairing allows primer extension to take place. Such complementarity need not be perfect. Thus, by "complementary" or "substantially complementary" herein is meant that the probes are sufficiently complementary to the target sequences to hybridize under normal reaction conditions. Deviations from perfect complementary are permissible so long as deviations are not sufficient to completely preclude hybridization. However, if the number of alterations or mutations is sufficient such that no hybridization can occur under the least stringent of hybridization conditions, as defined below, the sequence is not a complementary target sequence.

The primers of the present invention comprise nucleic acids. By "nucleic acid" or "oligonucleotide" or grammatical equivalents herein is meant at least two nucleotides covalently linked together. A nucleic acid of the present invention will generally contain phosphodiester bonds, although in some cases, nucleic acid analogs are included that may have alternate backbones, comprising, for example, phosphoramide (Beaucage, S. L. et al., Tetrahedron 49: 1925-1963 (1993) and references therein; Letsinger, R. L. et al., J. Org. Chem. 35: 3800-3803 (1970); Sprinzl, M. et al., Eur. J. Biochem. 81: 579-589 (1977); Letsinger, R. L. et al., Nucleic Acids Res. 14: 3487-3499 (1986); Sawai et al., Chem. Lett. 805 (1984); Letsinger, R. L. et al., J. Am. Chem. Soc. 110: 4470 (1988); and Pauwels et al., Chemica Scripta 26:141-149 (1986)), phosphorothioate (Mag, M. et al., Nucleic Acids Res. 19: 1437-1441 (199); and U.S. Pat. No. 5,644,048), phosphorodithioate (Briu et al., J. Am. Chem. Soc. 111: 2321 (1989)), O-methylphosphoroamidite linkages (see Eckstein, F., Oligonucleotides and Analogues: A Practical Approach, Oxford University Press, 1991), and peptide nucleic acid backbones and linkages (Egholm, M. Am. Chem. Soc. 114: 1895-1897 (1992); Meier et al., Chem. Int. Ed. Engl. 31: 1008 (1992); Egholm, M Nature 365: 566-568 (1993); Carlsson, C. et al. Nature 380: 207 (1996), all of which are incorporated by reference). Other analog nucleic acids include those with positive backbones (Dempcy, R. O. et al., Proc. Natl. Acad. Sci. USA 92: 6097-6101 (1995)); non-ionic backbones (U.S. Pat. Nos. 5,386,023; 5,637,684; 5,602,240; 5,216,141; and 4,469,863; Kiedrowshi et al., Angew. Chem. Intl. (Ed. English) 30: 423 (1991); Letsinger, R. L. et al., J. Am. Chem. Soc. 110: 4470 (1988); Letsinger, R. L. et al., Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4: 395 (1994); Jeffs et al., J. Biomolecular NMR 34: 17 (1994); Tetrahedron Lett. 37: 743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. 169-176 (1995)); all citations are hereby expressly incorporated by reference.

In a preferred embodiment, the nucleic acids are peptide nucleic acids (PNA), which includes peptide nucleic acid analogs. These backbones are substantially non-ionic under neutral conditions, in contrast to the highly charged phosphodiester backbone of naturally occurring nucleic acids. This results in several advantages. The PNA backbone exhibits improved hybridization kinetics. PNAs have larger changes in the melting temperature ($T_m$) for mismatched versus perfectly matched basepairs. DNA and RNA typically exhibit a 2-4.degree. C. drop in $T_m$ for an internal mismatch while with the non-ionic PNA backbone, the drop is closer to 7-9.degree. C. Similarly, due to their non-ionic nature, hybridization of the bases attached to these backbones is relatively insensitive to salt concentration. Particularly preferred are PNA derivatives extendible by polymerase. These primers comprise PNA oligomers with an attached nucleotide that is recognized and extended by a polymerase (see Lutz, M. J. et al., Nucleosides Nucleotides 18: 393-401 (1999) and Misra, H. S. Biochemistry 37: 1917-1925 (1998); publications hereby incorporated by reference). PNAs with a nucleotide or dinucleotide 3' terminus are recognized and extended by several polymerases, and the presence of the PNA segment will render the PNA-modified strand resistant to nuclease, particularly a 5'-3' exonuclease.

Although primers are generally single stranded, the nucleic acids as described herein may be single stranded or double stranded, as specified, or contain portions of both double stranded or single stranded sequence. The nucleic acid may be DNA, RNA, or hybrid, where the nucleic acid contains any combination of deoxyribo- and ribonucleotides, and any combination of bases, including uracil, adenine, thymine, cytosine, guanine, xanthine hypoxanthine, isocytosine, isoguanine, inosine, etc., although generally occurring bases are preferred. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid (PNA), each containing a base, are referred herein as a nucleotide.

As will be appreciated by those in the art, all of these nucleic acid analogs may find use in the present invention. In addition, mixtures of naturally occurring nucleic acids and analogs or mixtures of different nucleic acid analogs may be made.

The size of the primer nucleic acid may vary, as will be appreciated by those in the art, in general varying from 5 to 500 nucleotides in length, with primers of between 10 and 100 being preferred, between 12 and 75 being particularly preferred, and from 15 to 50 being especially preferred, depending on the use, required specificity, and the amplification technique.

Generally, the compositions of the present invention provide for a first primer which hybridizes to a first single strand of the target nucleic acid and a second primer which hybridizes to a second single strand of the target nucleic acid, where the first and second strands are substantially complementary. The primers are capable of primer extension by polymerase when hybridized to their respective strands. That is, the primers hybridized to the target nucleic acid have their 3' terminal nucleotide residues complementary to the nucleotide residue on the target nucleic acid such that the primers are capable of primer extension.

In one preferred embodiment, at least one of the primers further comprises at least one altered or mutated nucleotide residue, which produces a mismatch between the altered residue and the 3' terminal nucleotide of the other primer when the primers hybridize to each other. By "altered", "changed", or "mutated" nucleotide residue herein is meant any change in the nucleotide residue of the primer, such as transversions and transitions, to generate the required mismatch. The presence of a mismatch at the 3' terminal nucleotide blocks extension by polymerase, thus limiting non-target nucleic acid dependent extension reactions.

Accordingly, in one preferred embodiment, at least one nucleotide of the first primer is altered to produce a mismatch between the altered residue and the 3' terminal nucleotide residue of the second primer when the first and second primers hybridize to each other.

For any primer pair, the ability of the primers to hybridize to each other may be examined by aligning the sequence of the first primer to the second primer. The stability of the hybrids, especially the thermal melting temperature ($T_m$), may be determined by the methods described below and by methods well known in the art. These include, but are not limited to, nearest-neighbor thermodynamic calculations (see Breslauer, T. et al., Proc. Natl. Acad. Sci. USA 83: 8893-8897 (1986); Wetmur, J. G. Crit. Rev. Biochem. Mol. Biol. 26: 227-259 (1991); Rychlik, W. et al., J. NIH Res. 6: 78 (1994)); Wallace Rule estimations (Suggs, S. V. et al, "Use of Synthetic oligodeoxyribonucleotides for the isolation of specific cloned DNA sequences," Developmental biology using purified genes, D. B. Brown, ed., pp 683-693, Academic Press, New York, 1981), and $T_m$ estimations based on Bolton and McCarthy (see Baldino, F. J. et al., Methods Enzymol. 168: 761-777 (1989); Sambrook, J. et al., Molecular Cloning: A Laboratory Manual, Chapter 10, Cold Spring Harbor Laboratory Press, Cold Spring Harbor, N.Y., 2001). All references are hereby expressly incorporated by reference. The effect of various parameters including, among others, ionic strength, probe length, G/C content, and mismatches are taken into consideration when assessing hybrid stability. Consideration of these factors are well known to those skilled in the art (Sambrook, J., supra).

Whether the hybrids formed between the primers are capable of non-template dependent extensions by polymerase is assessed by the presence of complementarity at the 3' terminal regions of the hybrids. Those hybrids capable of being extended by polymerase have at least the 3' terminal nucleotide of at least one of the primers complementary to the nucleotide sequence of the other primer (Watson, R. Amplifications 5-6 (1989)). Thus, hybrids comprising complementarity of at least the 3' terminal nucleotide of at least one of the primers is selected for alteration or mutation of the primer sequences. Since primer extension by polymerase is less efficient when there is a mismatch near the 3' terminal nucleotide, alterations are preferred for primer hybrids with at least 2 or more nucleotides, and most preferably for hybrids with 3 or more complementary nucleotides at the 3' terminal region. Identifying hybrids with complementarity at 3' terminal regions may also be done using various algorithms, for example Amplify 1.2 software (University of Wisconsin, Department of Genetics, Madison, Wis.).

Alternatively, the presence of non-target nucleic acid dependent primer extension products are readily assessed by conducting amplification reactions in the absence of target nucleic acid and examining the products for primer-dimer species, for example by electrophoresis. By "primer-dimer" as used herein is meant non-target nucleic acid dependent extensions by polymerase arising from primers hybridized to other primers. The presence of primer-dimer products may also be assessed by conducting the amplification reaction in the absence or presence of target nucleic acid and analyzing the melting curves of the amplification products (see Ririe, K. M. Anal. Biochem. 245: 154-160 (1997); incorporated by reference).

In a preferred embodiment, the altered or mutated nucleotide residue is sufficiently distant from the 3' terminus of the primer to permit efficient extension by polymerase when primers hybridize to their respective strands of the target nucleic acid. Since it is well known that mismatches at or near the 3' terminal nucleotide can interfere with primer extension, the altered nucleotide residue is at least 1 or more residues from the 3' terminal nucleotide of the altered primer. More preferably, the altered residue is at least 2 or more residues, while in the most preferred embodiment, the altered residue is at least 3 or more residues from the 3' terminal nucleotide.

In another preferred embodiment of the present invention, both primers used in, the amplification reaction comprise at least one altered nucleotide residue such that hybridization of primers to each other generates mismatches at the 3' terminal residues of both primers to prevent extension by polymerase. This situation arises when each of the primers have 3' terminal regions complementary to the other primer. Thus, in a preferred embodiment, in addition to at least one altered nucleotide residue on the first primer, at least one nucleotide residue on the second primer is altered to produce a mismatch between the altered residue on the second primer and the 3 terminal nucleotide of the first primer when the first and second primers hybridize to each other. As discussed above, the altered residue is preferably at least 1 nucleotide residue, more preferably at least 2 nucleotide residues, and most preferably at least 3 nucleotide residues from the 3' terminal nucleotide of the second primer. Since the 3' terminal nucleotide residues of the first and second primers are not altered, they remain capable of being extended by polymerase when the primers are hybridized to their respective strands of the target nucleic acid. Consequently, target nucleic acids are readily amplified while non-target nucleic acid products are not amplified.

Although the embodiments described above relate to two different primers capable of hybridizing to each other, there are circumstances where a primer will be complementary to itself, resulting in primer-dimer products of a single primer. Thus, the present invention is not limited to different primers but also applicable to self-complementary primers that give rise to primer-dimer products in amplification reactions.

In view of the general design of primers for limiting non-target nucleic acid dependent amplifications, the present invention further provides for compositions useful for amplifying a plurality of repetitive units in a repetitive region of a target nucleic acid. By "repetitive unit", "repeat unit", "repetitive element" or grammatical equivalents as used herein is meant a minimal nucleotide sequence which is reiterated or repeated in the repetitive region. The repetitive unit for amplification may comprise any repetitive sequence, with repetitive units of 1 or more nucleotides being preferred, more preferably repetitive units between 3 and 100 nucleotides, and most preferably repetitive units between 4 and 30 nucleotides. In general, these repetitive units are arranged in tandem fashion, although there may be non-repetitive nucleotides present between the repetitive units. By "plurality" of repetitive elements herein is meant at least two or more repetitive units in the repetitive region. The repetitive regions may comprise those existing in nature, such as repetitive regions comprising centromeres and telomeres, or they may comprise repetitive regions introduced into cells and organisms, for example by transfection, recombination, or site specific integration (e.g., retroviral delivery). The number of repetitive units amplified for each set of primers will depend on the length of the primer and the nucleotide length of the repetitive unit. As will be appreciated by those skilled in the art, primer sequences and primer lengths may be chosen based on stability and specificity of the primer for the repetitive units.

In a preferred embodiment, the compositions for amplifying repetitive units of a repetitive region comprises a first primer which hybridizes to at least one repetitive unit on a first single strand of the target nucleic acid and a second primer which hybridizes to at least one repetitive unit on a second single strand of the target nucleic acid, where the first and second strands are substantially complementary. The primers are capable of primer extension when hybridized to their respective strands of the target nucleic acid. That is, the primers hybridized to the target nucleic acid have their 3' terminal nucleotide residues complementary to the nucleotide residue on the target nucleic acid such that the primers are capable of primer extension. In one aspect, at least one nucleotide residue of at least one of the primers is altered to produce mismatches with a nucleotide residue of at least one repetitive unit to which the primer hybridizes, wherein the altered nucleotide residue also produces a mismatch with the 3' terminal nucleotide residue of the other primer when the primers hybridize to each other, thus limiting primer extension of primer-primer hybrids.

Accordingly, in a preferred embodiment, at least one nucleotide residue of the first primer is altered to produce a mismatch between the altered residue and a nucleotide residue of at least one repetitive unit of the first strand to which the primer hybridizes, wherein the altered nucleotide residue also produces a mismatch with the 3' terminal nucleotide residue of the second primer when the first and second primers hybridize to each other.

The altered nucleotide residue is preferably at least 1 nucleotide residue, more preferably at least 2 nucleotide residues, and most preferably 3 nucleotide residues from the 3' terminal nucleotide to allow efficient extension by polymerase when the altered primer hybridizes to target nucleic acids.

In another aspect, both primers used for amplifying repetitive units comprise at least one altered nucleotide residue such that hybridization of primers to each other generates mismatches between the altered residues and the 3' terminal residues of both primers. Thus, in a preferred embodiment, in addition to the altered nucleotide residue on the first primer described above, at least one nucleotide residue of the second primer is altered to produce a mismatch between the altered residue and a nucleotide residue of at least one repetitive unit of the second strand to which the second primer hybridizes, wherein the altered residue on the second primer also produces a mismatch with the 3' terminal nucleotide of the first primer when the primers hybridize to each other.

In yet another preferred embodiment for amplifying repetitive units of a repetitive region, the present invention comprises a first primer which hybridizes to more than one repetitive unit on a first single strand of a target nucleic acid and a second primer which hybridizes to more than one repetitive unit on a second single strand of the target nucleic acid, where the first and second strands are substantially complementary. The primers are capable of primer extension when hybridized to their respective strands of the target nucleic acid, as described above. In one aspect, nucleotide residues of at least one of the primers are altered to produce mismatches between the altered residues and the nucleotide residues at the identical nucleotide position of each repetitive unit of the single strand of the target nucleic acid to which the primer hybridizes. These altered nucleotide residues also produce mismatches with the 3' terminal nucleotide residue of the other primer when the primers hybridize to each other, thus further limiting primer-extension of primer-primer hybrids.

Accordingly, in one preferred embodiment, nucleotide residues of the first primer is altered to produce mismatches between the altered residues and nucleotide residues at the identical nucleotide position of each repetitive unit of the first strand of the target nucleic acid to which the primer hybridizes. These altered nucleotides also produce mismatches with the 3' terminal nucleotide residue of the second primer when first second primer hybridize to each other.

The altered nucleotide residues are preferably at least 1 nucleotide residue, more preferably at least 2 nucleotide residues, and most preferably 3 nucleotide residues from the 3' terminal nucleotide to allow efficient extension by polymerase when the altered primer hybridizes to target nucleic acids.

In another aspect, both primers comprise altered nucleotide residues such that hybridization of primers to each other result in mismatches of the 3' terminal nucleotide of both primers. Thus, in a preferred embodiment, in addition to the altered nucleotide residues on the first primer, nucleotide residues on the second primer are altered to produce mismatches between the altered residues of the second primer and nucleotide residues at the identical nucleotide position of each repetitive unit of the second strand to which the primer hybridizes. These altered nucleotides of the second primer also produce mismatches with the 3' terminal nucleotide residue of the first primer when the primers hybridize to each other.

Since primers hybridized to target nucleic acids must be capable of primer extension, alterations of the first and second primers must be on non-complementary nucleotides of the repetitive unit. Thus, in one aspect, when both the first and second primers comprise altered residues, the alterations are at adjacent nucleotide positions of the repetitive unit. In another aspect, the alterations are situated on non-adjacent nucleotide positions of the repetitive unit. In general, mismatches at adjacent nucleotide positions provide for the most number of base paired or complementary residues between the altered nucleotide and the 3' terminal nucleotide, which may be important for efficiently amplifying short repetitive sequences (i.e., 3-6 basepairs).

In another preferred embodiment, the first and second primers further comprise a 5' terminal region that does not hybridize (i.e., basepair) with the target nucleic acid. The unpaired region comprises one or more nucleotides, with a preferred range of 3 to 60 nucleotides, and a most preferred range of 4 to 30 nucleotides. When the primers are directed towards amplification of repetitive units of a repetitive region, the 5' unpaired region blocks the 3' ends of the replicated primer extension products from initiating nucleic acid synthesis from the internal repetitive units of the amplification products during subsequent amplification cycles.

Although the 5' terminal unpaired region may be of any sequence which does not hybridize to the target nucleic acid, in a preferred embodiment the unpaired region comprises restriction sites, unique sequences for purposes of sequencing or primer extension reactions (i.e. amplification), or tag sequences for detecting and measuring the amplified product.

In a preferred embodiment, the primers of the present invention are designed to have similar $T_m$s. As used herein, primers with similar $T_m$s have a $T_m$ difference of about 10° C. or less, preferably 5° C. or less, and more preferably 2° C. or less. Use of primer sets (e.g., primer pairs) with similar or identical $T_m$s allow use of an annealing/extension temperature optimal for both primers and provides similar amplification efficiency at a particular amplification condition. Advantages are the ability to use similar concentrations of primers, particularly at lower concentrations, which limits generation of unwanted amplification products. By comparison, when $T_m$s of the primers are dissimilar, one primer is used at a higher concentration to compensate for differences in amplification efficiency. This higher primer concentration results in undesirable amplification products at a lower number of PCR cycles.

In one aspect, primers with similar $T_m$s are made by altering the length of primers or by selecting primers having similar guanosine-cytosine (GC) content. $T_m$s are assessed by the methods described above. As used herein, a "similar GC content" is meant a primer set which has a GC content difference of about 10% or less, more preferably a difference of about 5% or less, and most preferably a difference of about 2% or less, such that the primers display similar $T_m$s, as defined above. In the primer design process, $T_m$ and/or GC content is initially assessed for the region that hybridizes to the target nucleic acid. For primers with a non-hybridizing 5' terminal region described above, additional analysis of the $T_m$ and GC content is conducted for the entire primer sequence. Generally, primers are designed to have higher similarities of GC content at the 3' terminal region since it is this region that is extended by polymerase.

The primers of the present invention may be used to amplify various target nucleic acids. A single primer set, for example a primer pair, may be used to amplify a single target nucleic acid, or multiple primer sets may be used to amplify a plurality of target nucleic acids. Amplifications may be conducted separately for each unique primer set, or in a single reaction vessel using combinations of primer sets, generally known in the art as multiplexing. When multiple primer sets are used in a single reaction, primers are designed to limit formation of undesirable products and limit interference between primers of each primer set.

As the present invention relates to amplifying target nucleic acids with the primers described above, the present invention further provides for methods of amplifying target nucleic acid sequences. In a preferred embodiment, the method comprises contacting a target nucleic acid comprising substantially complementary first and second strands with the first and second primers described above, and amplifying the target nucleic acid by polymerase chain reaction.

By "target nucleic acid" or "target sequence" or grammatical equivalents herein is meant a nucleic acid sequence on a double or single stranded nucleic acid. The target sequence may be a portion of a gene, a regulatory sequence, genomic DNA, cDNA, RNA, including mRNA and rRNA, or other nucleic acids. It may be any length, with the understanding that longer sequences are more specific. In some embodiments, it may be desirable to fragment or cleave the sample nucleic acid into fragments of 100-10,000 base pairs, with fragments of roughly 500 basepairs being preferred in some embodiments. Fragmentation or cleavage may be done in any number of ways well known to those skilled in the art, including mechanical, chemical, and enzymatic methods. Thus, the nucleic acids may be subjected to sonication, French press, shearing, or treated with nucleases (e.g., DNase, restriction enzymes, RNase, etc.), or chemical cleavage agents (e.g., acid/piperidein, hydrazine/piperidine, iron-EDTA complexes, 1,10-phenanthroline-copper complexes, etc.).

As will be appreciated by those skilled in the art, the target sequence may take many forms. For example it may be contained within a larger nucleic acid sequence, i.e., all or part of a gene or mRNA, a restriction fragment of a plasmid or genomic DNA, among others. The sample comprising the target sequence may be obtained from any tissue of any organism, including blood, brain, bone marrow, lymph, liver, spleen, breast, epithelia (e.g., skin, mouth, etc.), or other tissues, including those obtained from biopsy. The samples may also comprise bodily excretions or fluids, such as saliva, urine, feces, cerebrospinal fluid, semen, milk etc. Other sources of target nucleic acids include bacteria, yeast, plant, virus, or other nucleic acid containing organisms, pathogenic or nonpathogenic. The nucleic acid can also be any nucleic acid generated artificially by chemical or enzymatic processes, such as PCR reactions.

The target sequence may be prepared using well known techniques. For instance, the sample may be treated using detergents, sonication, electroporation, denaturants, etc., to disrupt the cells, bacteria, or viruses. The target nucleic acids may be purified as needed. Components of the reaction may be added simultaneously, or sequentially, in any order as outlined below. In addition, a variety of agents may be added to the reaction to facilitate optimal hybridization, amplification, and detection. These include salts, buffers, neutral proteins, detergents etc. Other agents may be added to improve efficiency of the reaction, such as protease inhibitors, nuclease inhibitors, ant-microbial agents, etc., depending on the sample preparation methods and purity of the target nucleic acid. When the target nucleic acid is RNA, these nucleic acids may be converted to DNA, for example by treatment with reverse transcriptase (e.g., MoMuLV reverse transcriptase, Tth reverse transcriptase, etc.), as is well known in the art.

When the target nucleic acids are double stranded nucleic acids, they are denatured to generate a first single strand and a second single strand so as to allow hybridization of the primers. Any number of denaturation steps may be used such as temperature to about 95° C. although alkaline pH, denaturants (e.g., formamide), and other techniques may be applied as appropriate to the nature of the double stranded nucleic acid.

The primers are contacted with the target nucleic acid so that a first primer is capable of hybridizing to a first strand and a second primer is capable of hybridizing to a second strand of the target nucleic acid. A variety of hybridization conditions may be used to form the hybrids, including high, moderate, and low stringency conditions (see for example, Sambrook, J., Molecular Cloning: A Laboratory Manual, 3rd ed., Cold Spring Harbor Laboratory Press, Cold Spring Harbor, N.Y., 2001; Ausubel, F. M. et al., Current Protocols in Molecular Biology, John Wiley & Sons, updates to 2001; all of which are hereby incorporated by reference). Stringency conditions are sequence-dependent and will be different in different circumstances, including length of primer, number of mismatches, G/C content, and ionic strength. A guide to hybridization of nucleic acids is provided in Tijssen, P., "Overview of Principles of Hybridization and the Strategy of Nucleic Acid Assays," in Laboratory Techniques in Biochemistry and Molecular Biology: Hybridization with Nucleic Acid Probes, Vol. 24, Elsevier, Amsterdam, 1993). Generally, stringent conditions are selected to be about 5-10.degree. C. lower than the thermal melting point ($T_m$) for a specific hybrid at a defined solution condition (e.g., ionic strength, pH, concentration of nucleic acid). The $T_m$ is defined as the temperature under a defined solution condition at which 50% of the primer sequences complementary to the target nucleic acid are hybridized, or single stranded, at equilibrium. Generally, the solution condition is the solution conditions used for amplifying the target nucleic acids. Since the degree of stringency is generally the difference in the temperature of hybridization and the $T_m$, the degree of stringency may be maintained despite changes in solution condition of hybridization as long as the difference in temperature from $T_m$ is maintained. The hybridization conditions may also vary with the type of nucleic acid backbone, for example ribonucleic acid or peptide nucleic acid (PNA) backbone.

In hybridizing the primers to the target nucleic acids and in the amplification reactions, the assays are generally done under stringency conditions that allow formation of the hybrids in the presence of target nucleic acid. Those skilled in the art can alter the parameters of temperature, salt concentration, pH, organic solvent, chaotropic agents, or other variables to control the stringency of hybridization and also minimize hybridization of primers to non-specific targets (e.g., by use of "hot start" PCR or "touchdown" PCR).

Following contacting the primers to the target nucleic acids, the reaction is treated with an amplification enzyme, generally a polymerase. A variety of suitable polymerases are well known in the art, including, among others, Taq polymerase, KlenTaq, Tfl polymerase, DynaZyme, etc. Generally, although all polymerases are applicable to the present invention, preferred polymerases are thermostable polymerases lacking 3' to 5' exonuclease activity since use of polymerases with strong 3' to 5' exonuclease activity tends to remove the mismatched 3' terminal nucleotides. Also useful are polymerases engineered to have reduced or non-functional 3' to 5' exonuclease activities (e.g., Pfu(exo-), Vent(exo-), Pyra (exo-), etc.). Also applicable are mixtures of polymerases used to optimally extend hybridized primers. In another aspect, polymerase enzymes useful for the present invention are formulated to become active only at temperatures suitable for amplification. Presence of polymerase inhibiting antibodies, which become inactivated at amplification temperatures, or sequestering the enzymes in a form rendering it unavailable until amplification temperatures are reached, are all suitable. These polymerase formulations allow mixing all components in a single reaction vessel while preventing priming of non-target nucleic acid sequences.

In another aspect, those skilled in the art will appreciate that various agents may be added to the reaction to increase processivity of the polymerase, stabilize the polymerase from inactivation, decrease non-specific hybridization of the primers, or increase efficiency of replication. Such additives include, but are not limited to, dimethyl sulfoxide, formamide, acetamide, glycerol, polyethylene glycol, or proteinaceous agents such as E. coli. single stranded DNA binding protein, T4 gene 32 protein, bovine serum albumin, gelatin, etc. In another aspect, the person skilled in the art can use various nucleotide analogs for amplification of particular types of sequences, for example GC rich or repeating sequences. These analogs include, among others, c.sup.7-dGTP, hydroxymethyl-dUTP, dITP, 7-deaza-dGTP, etc.

Amplification reactions are carried out according to procedures well known in the art. Procedures for polymerase chain reaction are widely used and described (see for example, U.S. Pat. Nos. 4,683,195 and 4,683,202; hereby incorporated by reference). In brief, a double stranded target nucleic acid is denatured, generally by incubating at a temperature sufficient to denature the strands, and then incubated in the presence of excess primers, which hybridizes (i.e., anneals) to the single-stranded target nucleic acids. A DNA polymerase extends the hybridized primer, generating a new copy of the target nucleic acid. The resulting duplex is denatured and the hybridization and extension steps are repeated. By reiterating the steps of denaturation, annealing, and extension in the presence of a second primer for the complementary target strand, the target nucleic acid encompassed by the two primers is exponentially amplified. The time and temperature of the primer extension step will depend on the polymerase, length of target nucleic acid being amplified, and primer sequence employed for the amplification. The number of reiterative steps required to sufficiently amplify the target nucleic acid will depend on the efficiency of amplification for each cycle and the starting copy number of the target nucleic acid. As is well known in the art, these parameters can be adjusted by the skilled artisan to effectuate a desired level of amplification. Those skilled in the art will understand that the present invention is not limited by variations in times, temperatures, buffer conditions, and amplification cycles applied in the amplification process.

The products of the amplification are detected and analyzed by methods well known in the art. Amplified products may be analyzed following separation and/or purification of the products, or by direct measurement of product formed in the amplification reaction. Separation and purification methods include, among others, electrophoresis, including capillary electrophoresis (e.g., in agarose or acrylamide gels); chromatography (e.g., affinity, molecular sieve, reverse phase, etc.); and hybridization. The purified products may be subjected to further amplifications as is well known in the art. For detection, the product may be identified indirectly with fluorescent compounds, for example with ethidium bromide or SYBR™ Green, or by hybridization with labeled nucleic acid probes. Alternatively, labeled primers or labeled nucleotides are used in the amplification reaction to label the amplification product. The label comprises any detectable moiety, including fluorescent labels, radioactive labels, electronic labels, and indirect labels such as biotin or digoxigenin. When indirect labels are used, a secondary binding agent that binds the indirect label is used to detect the presence of the amplification product. These secondary binding agents may comprise antibodies, haptens, or other binding partners (e.g., avidin) that bind to the indirect labels. Secondary binding agents are preferably labeled with fluorescent moieties, radioactive moieties, enzymes, etc.

In another preferred embodiment, the amplification product may be detected and quantitated during the amplification reaction by real time quantitative PCR, variations of which are well known in the art. For instance, the TaqMan system uses a probe primer which hybridizes to sequences in an internal sequence within the nucleic acid segment encompassed by the primers used to amplify the target nucleic acid (Heid, C. A. et al., Genome Res. 6: 986-994 (1996); Holland, P. M. et al., Proc. Natl. Acad. Sci. USA 88: 7276-7280 (1991); incorporated by reference). This probe is labeled with two different fluorescent dyes (i.e., dual-labeled fluorogenic oligonucleotide probe), the 5' terminus reporter dye (TAMRA) and the 3' terminus fluorescence quenching dye (FAM). Cleavage of the probe by the 5' to 3' exonuclease activity of DNA polymerase during the extension phase of PCR releases the fluorogenic molecule from proximity of the quencher, thus resulting in increased fluorescence intensity.

In another aspect, real time quantitative PCR may be based on fluorescence resonance energy transfer (FRET) between hybridization probes (Wittwer, C. T. Biotechniques 22: 130-138 (1997); incorporated by reference). In this method, two oligonucleotide probes hybridize to adjacent regions of the target nucleic acid sequence. The upstream probe is labeled at the 3' terminus with an excitor dye (e.g., FITC) while the adjacently hybridizing downstream probe is labeled at the 5' terminus with a reporter dye. Hybridization of the two probes to the amplified target nucleic acid sequences positions the two dyes in close spatial proximity sufficient for FRET to occur. This allows monitoring the quantity of amplified product during the polymerase chain reaction. A similar approach is used in the molecular beacon probes (Tyagi, S, Nat. Biotechnol. 16: 49-53 (1998); incorporated by reference).

Molecular beacons are oligonucleotide probes comprising a quencher dye and a reporter dye at the opposite ends of a PCR product specific oligonucleotide. The dyes may also function based on FRET, and therefore may also be comprised of an excitation dye and a reporter dye. Short complementary segments at the 5' and 3' terminal regions allow for formation of a stem-loop structure, which positions the dyes at the terminal ends of the oligonucleotide into close proximity, thus resulting in fluorescence quenching or FRET. When the oligonucleotide hybridizes to a PCR product through complementary sequences in the internal region of the molecular beacon probe, fluorescence of the oligonucleotide probe is affected, thus allowing monitoring of product synthesis.

Real time quantitative PCR may also use fluorescent dyes that preferentially bind to double stranded nucleic acid amplification products during the PCR reaction, thereby providing continuous monitoring of product synthesis (see Higuchi, R. et al., Biotechnology 11: 1026-1030 (1993); Morrison, T. B. et al., Biotechniques 24: 954-962 (1998)). Suitable fluorescent dyes include, among others, ethidium bromide, YO PRO-1™ (Ishiguro, T. Anal Biochem. 229: 207-213 (1995)), and SYBR™. Green dyes (Molecular Probes, Eugene, Oreg., USA). When amplifying target nucleic acids comprising repetitive regions, FRET or molecular beacon based probes are not preferred if FRET or molecular beacon probes are directed to repetitive units since they will hybridize to repetitive sequences on the primers, thereby failing to distinguish between primers and amplified product.

In a further preferred embodiment; real time quantitative PCR is accomplished with primers containing a single fluorophore attached near the 3' terminal nucleotide (Nazarenko, I. et al., Nucleic Acids Res. 30: e37 (2002); Nazarenko, I. et al., Nucleic Acids Res. 30: 2089-2195 (2002); LUX™ Fluorogenic Primers, Invitrogen, Palo Alto, Calif.; hereby incorporated by reference). The 5' end of these primers have a 5 to 7 nucleotide extension capable of hybridizing to the 3' terminal region to generate a blunt-ended hairpin (i.e., stem-loop) structure, whose formation results in fluorescence quenching of the fluorophore. When the primer forms a duplex, for example by primer extension on a template, the quenching is reduced or eliminated, thus providing a measure of PCR product in the sample. Because only a single fluorophore is used, different fluorophores may be used and detected in a single reaction. Consequently, these primers are useful for amplification and detection of a plurality of different target nucleic acids in a single reaction vessel by use of different primer sets with distinguishable fluorophores. As discussed herein, various target nucleic acids include combinations of single copy genes and repetitive sequences.

Instrumentation suitable for real time monitoring of PCR reactions are available for use in quantitative PCR methods (ABI Prism 7700, Applied Biosystems Division, Perkin Elmer, Fosters City, Calif., USA; LightCycler™, Roche Molecular Biochemicals, Indianapolis, Ind., USA).

When real time quantitative PCR is used to detect and measure the amplification products, various algorithms are used to calculate the number of target nucleic acids in the samples (see ABI Prism 7700 Software Version 1.7; Lightcycler™ Software Version 3; incorporated by reference). Quantitation may involve use of standard samples with known copy number of the target nucleic acid and generation of standard curves from the logarithms of the standards and the cycle of threshold ($C_t$). In general, $C_t$ is the PCR cycle or fractional PCR cycle where the fluorescence generated by the amplification product is several deviations above the baseline fluorescence (Higuchi, R. et al., supra). Real time quantitative PCR provides a linearity of about 7 to 8 orders of magnitude, which allows measurement of copy number of target nucleic acids over a wide dynamic range. The absolute number of target nucleic acid copies can be derived from comparing the $C_t$ values of the standard curve and the samples.

The copy number of target nucleic acids may also be determined by comparative quantitative real time PCR. Use of nucleic acids of known copy number or consistent copy number allows quantitating the copy number of target nucleic acids in a sample. The standard may be a single copy gene, a nucleic acid of known copy number, or when quantitating RNA copy number, a constitutively expressed housekeeping gene (see Johnson, M. R. Anal. Biochem. 278: 175-184 (2000); Boulay, J.-L., et al., Biotechniques 27: 228-232 (1999)).

The compositions and methods described above find use in any process for amplifying target nucleic acids by polymerase chain reaction. Thus, the present invention is useful in detecting and monitoring infectious diseases, for example in testing for presence of pathogenic bacteria and viruses (e.g., viral load). For instance, target viral nucleic acids include, without limitation, HIV, HCV cytomegalovirus, hepatitis, etc. The present invention is also applicable for monitoring medical therapies. For example this may involve monitoring the progress of bacterial infections following antibiotic administration.

The present invention finds applications in characterizing the functional state of cells, especially for cell changes associated with disease states. For example, amplification of particular genetic segments during cancer progression in ovarian or breast cancer is correlated not only with the stage of the cancer but also survival rates (see Kalioniemi, A et al., Proc. Natl. Acad. Sci. USA 91: 2156-2160 (1994)). Thus, quantitation of gene amplification has diagnostic and prognostic value for a variety of tumors (Kawate, S. et al., Oncology 57: 157-163 (1999); Biechi, I. et al., Int. J. Cancer 78: 661-666 (1998)). Conversely, loss of genetic elements (i.e., loss of heterozygosity or microsatellite instability) is also associated with particular disease states, thus providing a useful focal point for disease diagnostics. For example, deletions of chromosomal region 18q21 is frequently observed in colorectal cancers while the tumor suppressor p53 gene located on chromosome 17p13.1 is frequently deleted in a variety of cancer types (Largey, J. S. et al., Cancer 17: 1933-1937 (1993)).

Of particular importance in cell function and disease are repetitive sequences, especially tandemly repetitive sequences found in genomes of many organisms. In eukaryotes, these sequences are generally classified into three major categories: satellite, minisatellite, and microsatellite. Satellite DNAs have repeat lengths of about 1 to several thousand bases and can constitute repetitive regions of up to 100 million basepair clusters, for example in heterochromatic regions of eukaryotic chromosomes. These sequences are mainly associated with centromeres and telomeres. Minisatellite sequences are moderately repetitive, tandemly repeated arrays of about 9-100 basepair repeats, generally having mean array lengths of about 0.5 to 30 kb. These are generally found in euchromatic regions and are highly variable in size. Microsatellites are moderately repetitive arrays of short (i.e., about 2-6 basepairs) repeats. Copy numbers of these repeats vary within a population, typically having mean array sizes of about 10 to 100 bases. In many cases, changes in the extent of repeats is often correlated with certain diseases. For example, increase in the copy number of triplet repeats CGG, CTG, and GAA is associated with Huntington's disease, Fragile X syndrome, and myotonic dystrophy. The extent of the expansion of these triplet repeats is often associated with the severity or onset of the disease state such that progeny inheriting the expanded repeats have more severe disorders or, where the disorder is not congenital, an earlier age of onset. Disorders related to expansion of tandem repeat sequences is not limited to trinucleotide repeats and can involve larger repeating units (see Lafreniere, R. G. et al., Nat. Genet. 15: 298-302 (1997)).

Tandem repetitive sequences also have important biological functions. With the certain exceptions (e.g., budding yeast), the centromeres of most plants, animal and fungus have large arrays of tandem repetitive sequences. Although the physiological roles of these sequences are uncertain, it is believed that they function in the assembly of the kinetichore to ensure faithful and efficient chromosome segregation. Thus, determining the variability in the number of repeats can provide information about function and regulation of centromeres and diseases related to centromere dysfunction.

Of more defined importance in cell function are tandemly repeating sequences comprising the telomeres of linear eukaryotic chromosomes. Telomeric DNA or telomeric region is the chromosomal region located at the ends of chromosomes, consisting of tandem arrays of repetitive units of short sequences ranging from about 5 to 26 basepairs. The telomeric regions of different organisms differ in their repetitive unit or repeat sequence. These repeat sequences are known for a variety of organisms, including human and other mammals, *Tetrahymena*, yeast, *Drosophila*, and nematodes. In humans, the telomeric repetitive unit is 5'-TTAGGG-3' while the *Tetrahymena* repetitive unit is 5'-TTGGGG-3'.

The telomere repetitive unit not only varies between species as to the repeat sequence, but also as to number of repetitive units in an organism. It is well established that the length and integrity of telomeres is important for cell growth and proper segregation of chromosomes. For example, development of many types of cancers correlates with activation of telomere maintenance while cell senescence, a condition in which cells have lost the ability to replicate, although the normal replicative signals are present, correlate with loss of telomere integrity. For example, shortening of telomere induces proliferative senescence in cells while telomerase inhibition can lead to induced cell apoptosis (Zhang, X. et al., Genes Dev. 2388-2399 (1999)). Moreover, knockout of telomerase RNA in mice results in animals with developmental defects, age related pathologies, and increased cancer susceptibility (Rudolph, K. L. et al., Cell 96: 701-712 (1999); Herrera, E. et al., EMBO J. 18: 2950-2960 (1999)).

Thus, measuring the number of repetitive units of specific repetitive sequences find important applications, including, but not limited to, cancer diagnosis, diagnosis of aging related diseases, integrity of cloned organisms, screening of inherited disorders, and drug screening for agents directed to enzymes (i.e., telomerase) and cellular pathways regulating length of repetitive sequences.

Thus, in a preferred embodiment, the present invention provides for rapid analysis of telomere lengths by direct amplification of the repeat sequences using primers incapable of generating primer-dimers but capable of primer extension when hybridized to telomere repetitive units. Since the telomeres of various organisms have differing repetitive unit sequences, amplifying telomeres of a specific organism will employ primers specific to the repetitive unit of the organism. Human telomeric sequences are used herein to illustrate practice of the present invention for direct amplification and quantitation of tandemly repeated nucleic acid sequences, but is not limited to the specific embodiment described herein.

In determining the number of telomeric repetitive units, the selected primers are complementary to repetitive units of the repetitive region. The first primer has sequences complementary to telomeric repetitive sequences on a first single strand of the target nucleic acid, and a second primer has sequences complementary to the telomeric repetitive sequences on a second single strand of the target nucleic acid, wherein the first and second strands are substantially complementary. In one preferred embodiment, nucleotide residues of the first primer are altered to produce mismatches between the altered residues and nucleotide residues at the identical nucleotide position of each telomere repetitive unit of the first strand of the target nucleic acid. These altered residues also produce a mismatch with the 3' terminal nucleotide of the second primer when the primers hybridize to each other. In another preferred embodiment, the nucleotide residues of the second primer are also similarly altered such that hybridization primers to each other results in the first and second primers with mismatched 3' terminal nucleotides.

In the preferred embodiment, the altered nucleotide residues producing the mismatches are on both the first and second primers to limit formation any primer-dimer products. In this arrangement, the mismatches may be on adjacent or on non-adjacent nucleotide positions of the repetitive unit. Mismatches on adjacent nucleotide positions of the repetitive unit maximizes the number of basepaired residues from the 3' terminal nucleotide to the altered residue of each primer. An exemplification of primers for amplification of human telomere repetitive units are provided in FIG. 1.

Subsequent to contacting the first and second primers to the single stranded form of the repetitive region, the primers are extended polymerase, and the repetitive units amplified by reiterative cycles of denaturation, annealing, and extension. In a preferred embodiment, the 5' terminal region comprises non-basepairing sequences to restrict priming from internal repeats of amplified repetitive sequences.

The amplified products are quantitated as described above. In a preferred embodiment, real time quantitative PCR is used to determine the copy number of the telomere repetitive units in the target nucleic acid sample. Standards for determining and comparing telomere repetitive unit number include use of single copy genes (e.g., ribosomal phosphoprotein 364B) or a target nucleic acid of known copy number (e.g., a plasmid with known number of telomere repetitive units). By the methods described herein, the copy number of repetitive units of a large number of samples may be quantitated for purposes of determining the number of telomere repetitive units, and thus the average length of telomeres.

Measuring the number of repetitive units of telomeres has a wide variety of applications in medical diagnosis, disease prognosis, and therapeutics. The present invention is useful for determining telomere lengths of various types of cancer cells since activation of telomerase activity is associated with immortalization of cells. Cells can be analyzed over time to determine whether an increase, decrease, or stabilization of telomeres is associated with disease progression. Various cancer cell types amenable for testing include breast, liver, brain, bone, prostate, lymphocyte, melanoma, colon cancers, etc.

The present invention also finds use in diagnosis of diseases related to early onset of aging. For example, individuals with Hutchinson Gilford progeria disease show premature aging and reduction in proliferative potential in fibroblasts associated with loss of telomeric length (Alssopp, R. C. et al., Proc. Natl. Acad. Sci. USA 89: 10114-10118 (1992)) while patients with dyskeratosis congenita display progressive bone-marrow failure, abnormal skin pigmentation, leukoplakia, and nail dystrophy because of a deletion of telomerase RNA (see Vulliamy, T. Nature 413: 432-435 (2001)). Thus, amplification and quantitation of the number of telomeric repeats is useful for determining the association of particular diseases with changes in telomere length.

In another preferred embodiment, the present invention is useful in monitoring effectiveness of therapeutics or in screening for drug candidates affecting telomere length or telomerase activity. For example, the present invention finds use in monitoring the effectiveness of cancer therapy since the proliferative potential of cells may be related to the maintenance of telomere integrity. The ability to monitor telomere characteristics can provide a window for examining the effectiveness of particular therapies and pharmacological agents. In another aspect, the present invention finds use as a general method of screening for candidate drugs affecting biological pathways regulating telomere length, such as telomerase activity. Ability to rapidly amplify telomere repeats provides a high throughput screening method for identifying small molecules, candidate nucleic acids, and peptides agents affecting telomere characteristics in the cell.

It is understood by the skilled artisan that the steps for constructing the primers and the methods for amplifying target nucleic acid sequences can be varied according to the options provided herein. The following examples serve to more fully describe the manner of using and the best mode for the above described invention. It is also understood, however, that these embodiments in no way serve to limit the scope of the present invention and that those skilled in the art may modify according to the skill in the art. All references cited herein are incorporated by reference.

EXAMPLES

Example 1

Direct Amplification of Human Telomeric Repetitive Sequences

Genomic DNA was extracted from blood samples by standard procedures. The samples used to compare quantitative PCR vs. Southern blot approaches to telomere measurement were donated by 21 unrelated individuals (11 women and 10 men, age range 61-94 years) from Utah families that are part of the Centre pour les Etudes du Polymorphisme Humaine (CEPH) collection used worldwide for building the human genetic linkage map (White, R. et al., Nature 313: 101-105 (1985)). Purified DNA samples were diluted in 96-well microtiter source plates to approximately 1.75 ng/ul in 10 mM Tris-HCl, 0.1 mM EDTA, pH 7.5 (final volume 300 ul per well), heated to 95.degree. C. for 5 minutes in a thermal cycler, quick-chilled by transfer to an ice-water bath for 5 minutes, centrifuged briefly at 700.times.g, sealed with adhesive aluminum foil, and stored at 4.degree. C. until the time of assay.

Real time quantitative PCR on the extracted DNA samples are performed on separate 96 well plates. Two master mixes of PCR reagents were prepared, one with the telomere (T) primer pair, the other with the single copy gene (S) primer pair. Depending on the reaction conditions, 30 or 10 ul of T master mix was added to each sample well and standard curve well of the first plate, and 30 or 10 ul of S master mix was added to each sample well and standard curve well of the second plate. For each individual in whom the T/S ratio was assayed, three identical 20 ul aliquots of the DNA sample (35 ng per aliquot) were added to plate 1, and another three aliquots were added to the same well positions in plate 2. For each standard curve, one standard DNA sample was diluted serially in TE (10 mM Tris, 1 mM EDTA, pH 7.0) by .about.1.68-fold per dilution to produce five concentrations of DNA ranging from 0.63 ng/ul up to 5 ng/ul, which were then distributed in 20 ul aliquots to the standard curve wells on each plate. The plates were then sealed with a transparent adhesive cover, centrifuged briefly at 700×g, and stored at 4° C. in the dark until the PCR was performed (0-3 days later).

PCR amplification conditions depended on the primers used and the template DNA being amplified. In one set of experiments, telomere repeat sequences were amplified with primer set tel 1 (5'-GGTTTTTGAGGGTGAGGGTGAG-GGTGAGGGTGAGGGT-3') (SEQ ID NO: 1) and tel 2 (5'-TCCCGACTATCCCTATCCCTATCCC-TATCCCTATC-CCTA-3') (SEQ ID NO: 2). Concentrations of reagents in the PCR mixes were 150 nM 6-ROX and 0.2.times. SYBR™ Green I (Molecular Probes, Inc.); 15 mM Tris-HCl, pH 8.0; 50 mM KCl; 2 mM MgCl$_2$; 0.2 mM of each dNTP; 5 mM D17; 1% DMSO; 1.25 units of AmpliTaq Gold DNA polymerase (Applied Biosystems, Inc.); 270 nM of tel 1 primer; and 900 nM of tel 2 primer in a final volume of 50 ul. The thermal cycling profile began with a 95° C. incubation for 10 min. to activate the AmpliTaq Gold DNA polymerase followed by 18 cycles of 95° C.×15 s and 54° C.×2 min.

Alternatively, the telomere specific primer sequences were optimized to have similar $T_m$s, particularly by designing the primers to have similar or identical GC content. Each primer of primer set tel 1b: (5'-CG-GTTTGTTTGGGTTTGGGTTTGGGTTTGGGTTTGG GTT-3') (SEQ ID NO: 8) and tel 2b: (5'-GGCTTGCCTTAC-CCTTACCCTTACCCTTACCCTTACCCT-3') (SEQ ID NO: 9) carries a purposefully introduced single base substitution at the sixth base from the 3' end and at every sixth base thereafter in the 5' direction, for a total of five introduced base changes at every sixth position of the repeat sequence. When the primers hybridize to the target telomeric DNA, five single base mismatches result but the hybrids have perfect complementarity to the target telomeric DNA sequences in the last five bases at the 3' end of each primer. Hybridization of the primers to each other results in base-pairing at four out of six positions, and the 3' terminal residue of each primer forms a mismatch with the other primer. PCR conditions with these $T_m$ optimized primers were 0.4.times. Sybr Green I, 15 mM Tris-HCl, pH 8.0; 50 mM KCl; 1.5 mM MgCl$_2$, 1% DMSO, 2.5 mM DTT, 200 uM each dNTP, 0.75 Units of AmpliTaq Gold DNA polymerase, 450 nM of tel 1 b primer, and 450 nM of tel 2b primer, in a final volume of 30 ul per reaction. The thermal cycling profile was 95° C.×10 min. followed by 18 cycles of 95° C. for 15 sec. (denaturation) and 56° C. for 2 min. (anneal/extend). No ROX dye is needed for this assay condition. In general, three telomere PCR reactions were done on each experimental DNA. Each 96 well telomere PCR plate contained a row with 2 NTC wells (no genomic DNA), and 10 standard curve wells containing a serial dilution of a reference DNA to five concentrations, with each concentration in duplicate, ranging from 0.25 ng/microliter (final concentration) up to 2 ng/microliter (final concentration).

The 36B4 gene, which encodes acidic ribosomal phosphoprotein PO, was used to normalize the telomere signal (Boulay et al., Biotechniques 27: 228-232 (1999)). The primer set used was 36B4u (5'-CAGCAAGTGGGAAGGT-GTAATCC-3', SEQ ID NO: 6) and 36B4d, (5'-CCCATTC-TATCATCAACGGGTACAA-3', SEQ ID NO: 7). PCR conditions contained 150 nM 6-ROX and 0.2×SYBR™ Green I (Molecular Probes, Inc.); 15 mM Tris-HCl, pH 8.0; 50 mM KCl; 2 mM MgCl$_2$; 200 uM of each dNTP; 5 mM DTT; 1% DMSO; 1.25 units of AmpliTaq Gold DNA polymerase (Applied Biosystems, Inc.); 300 nM of 36B4u primer; and 500 nM. of 36B4d primer in a final volume of 50 ul per reaction.

The thermal cycling profile was 95° C. incubation for 10 min followed by 30 cycles of 95° C.×15 s, 58° C.×1 min. Alternatively, for optimal amplifications, the PCR reactions contained 0.4.times. Sybr Green I, 15 mM Tris-HCl, pH 8.0; 50 mM KCl; 3.5 mM $MgCl_2$, 1% DMSO, 2.5 mM DTT, 200 uM each dNTP, 0.75 Units of AmpliTaq Gold DNA polymerase, 300 nM of 36B4u primer, and 500 nM of 36B4d primer, in a final volume of 30 ul per reaction. The thermal cycling profile was 95° C.×10 min. followed by 30 cycles of 95° C. for 15 sec. (denaturation) and 56° C. for 1 min. (anneal/extend). No ROX dye was needed under the second set of conditions.

Similar to amplification of telomere repeats, three 36B4 PCR reactions were done on each experimental DNA sample. Each 96 well telomere PCR plate contained a row with 2 NTC wells (no genomic DNA), and 10 standard curve wells containing a serial dilution of a reference DNA to five concentrations, with each concentration in duplicate, ranging from 0.25 ng/microliter (final concentration) up to 2 ng/microliter (final concentration).

All PCRs were performed on ABI Prism 7700 Sequence Detection System (Applied Biosystems, Inc., Foster City, Calif., USA), a thermal cycler equipped to excite and read emissions from fluorescent molecules during each cycle of the PCR. ABPs SDS version 1.7 software was then used to generate the standard curve for each plate and to determine the dilution factors of standards corresponding to the T and S amounts in each sample.

In the presence of 35 ng of human DNA, a telomere PCR product was detectable by real time quantitative PCR beginning from about 9 cycles of PCR. Analysis of the product after 25 cycles by electrophoresis on agarose gels and staining with ethidium bromide shows a smear of products beginning from about 76 basepairs, which is equivalent to the sum of the lengths of the telomere specific primers (see FIG. 1), to products of about 400 base pairs (FIG. 4). The copy number of the PCR is proportional to the number of sites available for binding of the primer in the first cycle of the PCR. Omitting the genomic DNA results in no detectable amplification product after 25 cycles for either the telomere or single copy gene primers.

Example 2

Determining the Relative Telomere Length

Mean telomere restriction fragment (TRF) lengths were determined as described by Slagboom et al., Am. J. Hum. Genet. 55: 876-882 (1994), hereby incorporated by reference. Approximately 0.5 ug of purified whole blood DNA was digested to completion with Hae III restriction enzyme. Digested samples were then mixed with DNA size standards, separated by electrophoresis on agarose gels, and transferred to a nylon membrane. The membranes were hybridized with $^{32}P$ end labeled oligonucleotide, $(TTAGGG)_7$ (SEQ ID NO: 10) washed to remove non-specifically bound probe, exposed to a phosphor plate for 1 to 5 days, and the plates scanned with a PhosphorImager (Molecular Dynamics, Inc.). Blots were then stripped of the telomere probe, hybridized with radiolabeled probe for the DNA size standards, washed, exposed to a phosphor plate, and the plates scanned. The size standard images and telomere smear images were then superimposed to locate the positions of the size intervals within the telomere smears. Mean TRF length was then calculated as mean TRF length=$(\Sigma OD_i)/(\Sigma OD_i/L_i)$, where $OD_i$ is total radioactivity above background in interval i, and $L_i$ is the average length of i in basepairs. This entire procedure was performed twice; i.e., the two mean TRF length values determined on each individual were obtained from two independent experiments.

To measure the T/S value (telomere to single copy gene ratio), the $C_t$ value—the fractional cycle number at which the amplification sample's accumulating fluorescence crosses a set threshold value that is several standard deviations above background fluorescence—was determined for samples amplified with telomere specific (T) primers and single copy gene specific (S) primers. Since the amount of PCR product approximately doubles in each cycle of the PCR, the T/S ratio is approximately $[2^{Ct(telomeres)}/2^{Ct(single\ copy\ gene)}]^{-1} = 2^{-\Delta Ct}$. The average $\Delta C_t$ was −9.05 (see FIG. 2). That is, PCR of a single copy gene required about 9 more cycles than PCR of telomeres to produce equivalent fluorescent signal as measured by real time PCR. The standard deviation was 1.48%.

The relative T/S ratio, which is the T/S of one sample relative to the T/S of another sample, is expressed as $2^{-(\Delta Ct1 - \Delta Ct2)} = 2^{-\Delta\Delta Ct}$. This formula allows calculation of the relative T/S ratio of each sample. DNA samples of 21 unrelated patients were amplified and quantitated by real time quantitative PCR (see Experiment 2). Comparison of the relative T/S ratio calculated from PCR correlated well with the mean TRF lengths determined by Southern hybridization (see FIG. 3). The y intercept is about 3.6 kbp, which is approximately the mean length of the subtelomeric region between the restriction enzyme recognition sites and the beginning of the telomeric hexamer repeats (Hultdin, M. Nucleic Acids. Res. 26: 3651-3656 (1998)). Moreover, the observed average telomere length in whole blood as measured by relative T/S ratio varies over a 2.5 range among unrelated age and sex matched adults. This range of variability is in excellent agreement with other studies on the range of variation of TRF lengths in age matched adults if the average subtelomeric length of 3.4 kbp is subtracted from each reported mean TRF length (Hultdin, M. Nucleic Acids Res. 3651-3656 (1998); Vaziri, H. et al., Am. J. Hum. Genet. 52: 661-667 (1993)).

What is claimed is:

1. A method of diagnosing cancer comprising:
amplifying repetitive units in a repetitive region of a human target nucleic acid comprising:
  a) contacting a target nucleic acid comprising substantially complementary first and second strands with a first and a second primer, wherein said first primer hybridizes to at least one repetitive unit of said first strand and said second primer hybridizes to at least one repetitive unit of said second strand, wherein said hybridized primers are capable of primer extension when hybridized to their respective strands, and wherein at least one nucleotide of said first primer produces an internal base pair mismatch between said first primer and a nucleotide of said repetitive unit when said first primer is hybridized to at least one repetitive unit of said first strand, wherein said first primer also produces a mismatch with the 3' terminal nucleotide of said second primer when first and second primers hybridize to each other, wherein at least one nucleotide of said second primer produces an internal base pair mismatch between said second primer and a nucleotide of said repetitive unit when said second primer is hybridized to at least one repetitive unit of said second strand, wherein said second primer also produces a mismatch with the 3' terminal nucleotide of said first primer when first and second primers hybridize to each other;
  b) amplifying the target nucleic acid by the polymerase chain reaction;
  c) determining the number of repetitive units present in the target nucleic acid and comparing the number of repetitive units to a control; wherein a change in the number of repeats indicates the presence of cancer.

2. The method of claim 1, wherein nucleotides residues of said second primer produce internal base pair mismatches with nucleotides at the identical nucleotide positions of each repetitive unit of said second strand.

3. The method of claim 1, wherein said first and second primers further comprise 5' terminal sequences which do not hybridize to said repetitive units.

4. The method of claim 1, wherein at least two of the mismatches in the complex formed by hybridization of said first and said second primer are on adjacent nucleotide positions of said repetitive unit.

5. The method of claim 1, wherein said mismatches are on nonadjacent nucleotide positions of said repetitive unit.

6. The method of claim 1, wherein said repetitive unit comprises hexanucleotide repeats.

7. The method of claim 1, wherein said repetitive unit comprises pentanucleotide repeats.

8. The method of claim 1, wherein said repetitive unit comprise tetranucleotide repeats.

9. The method of claim 1, wherein said repetitive units comprise telomere repetitive units.

10. The method of claim 9, wherein said first primer comprises SEQ ID NO: 1 and said second primer comprises SEQ ID NO: 2.

11. The method of claim 9, wherein said first primer comprises SEQ ID NO: 8 and said second primer comprises SEQ ID NO: 9.

12. A method of diagnosing cell senescence comprising:
amplifying repetitive units in a repetitive region of a human target nucleic acid comprising:
  a) contacting a target nucleic acid comprising substantially complementary first and second strands with a first and a second primer, wherein said first primer hybridizes to at least one repetitive unit of said first strand and said second primer hybridizes to at least one repetitive unit of said second strand, wherein said hybridized primers are capable of primer extension when hybridized to their respective strands, and wherein at least one nucleotide of said first primer produces an internal base pair mismatch between said first primer and a nucleotide of said repetitive unit when said first primer is hybridized to at least one repetitive unit of said first strand, wherein said first primer also produces a mismatch with the 3' terminal nucleotide of said second primer when first and second primers hybridize to each other, wherein at least one nucleotide of said second primer produces an internal base pair mismatch between said second primer and a nucleotide of said repetitive unit when said second primer is hybridized to at least one repetitive unit of said second strand, wherein said second primer also produces a mismatch with the 3' terminal nucleotide of said first primer when first and second primers hybridize to each other;
  b) amplifying the target nucleic acid by the polymerase chain reaction;

c) determining the number of repetitive units present in the target nucleic acid and comparing the number of repetitive units to a control; wherein a decrease in the number of repeats indicates cell senescence; wherein said repetitive units comprise telomere repetitive units.

13. The method of claim 12, wherein nucleotides residues of said second primer produce internal base pair mismatches with nucleotides at the identical nucleotide positions of each repetitive unit of said second strand.

14. The method of claim 12, wherein said first and second primers further comprise 5' terminal sequences which do not hybridize to said repetitive units.

15. The method of claim 12, wherein at least two of the mismatches in the complex formed by hybridization of said first and said second primer are on adjacent nucleotide positions of said repetitive unit.

16. The method of claim 12, wherein said mismatches are on nonadjacent nucleotide positions of said repetitive unit.

17. The method of claim 12, wherein said repetitive unit comprises hexanucleotide repeats.

18. The method of claim 12, wherein said repetitive unit comprises pentanucleotide repeats.

19. The method of claim 12, wherein said repetitive unit comprise tetranucleotide repeats.

20. The method of claim 12, wherein said first primer comprises SEQ ID NO: 1 and said second primer comprises SEQ ID NO: 2.

21. The method of claim 12, wherein said first primer comprises SEQ ID NO: 8 and said second primer comprises SEQ ID NO: 9.

* * * * *